(12) United States Patent
Lin et al.

(10) Patent No.: US 6,289,243 B1
(45) Date of Patent: Sep. 11, 2001

(54) AUTOMATIC EXTERNAL CARDIOVERTER/ DEFIBRILLATOR WITH TACHYARRHYTHMIA DETECTOR USING A MODULATION (AMPLITUDE AND FREQUENCY) DOMAIN FUNCTION

(75) Inventors: Dongping Lin, Irvine; Raul Ybarra, Newhall; Prabodh Mathur, Laguna Niguel, all of CA (US)

(73) Assignee: Cardiac Science, Inc., Irvine, CA (US)

( * ) Notice: Subject to any disclaimer, the term of this patent is extended or adjusted under 35 U.S.C. 154(b) by 0 days.

(21) Appl. No.: 09/452,507

(22) Filed: Dec. 1, 1999

(51) Int. Cl.⁷ .................................................. A61N 1/39
(52) U.S. Cl. ........................................................ 607/5
(58) Field of Search ................................... 607/4, 5, 14

(56) References Cited

U.S. PATENT DOCUMENTS

| | | | |
|---|---|---|---|
| 3,703,900 | * 11/1972 | Holznagel | 607/5 |
| 4,523,595 | * 6/1985 | Zibell | 607/5 |
| 5,391,187 | * 2/1995 | Freeman | 607/5 |

* cited by examiner

Primary Examiner—George R. Evanisko
(74) Attorney, Agent, or Firm—Gottlieb, Rackman & Reisman, P.C.

(57) ABSTRACT

An external defibrillator includes a detector used to detect a life threatening condition of a patient, a controller operating the defibrillator automatically and a therapy delivery circuit that delivers appropriate therapy. Advantageously a parameter is derived from the cardiac signals sensed in the patient, the parameters being used to differentiate between shockable events such as ventricular tachyarrhythmia and other events such as SVT. The defibrillator is attached to a patient by an attendant and once it is attached, the defibrillator is adapted to monitor the patient and when a life threatening condition is detected, to apply therapy automatically, i.e., without any involvement by the patient or the attendant.

18 Claims, 14 Drawing Sheets

AUTOMATIC EXTERNAL CARDIOVERTER/ DEFIBRILLATOR WITH TACHYARRHYTHMIA DETECTOR USING A MODULATION (AMPLITUDE AND FREQUENCY) DOMAIN FUNCTION

BACKGROUND OF THE INVENTION

A. Field of Invention

This invention pertains to an external defibrillator arranged and constructed to provide anti-tachyarrhythmia therapy to a patient on demand. In particular, an automatic external cardioverter/defibrillator is described which has several operational modes including a fully automatic mode in which shocks are delivered without any manual intervention, an advisory mode and a manual mode. Moreover, the invention pertains to a defibrillator with an integral tachyarrhythmia detector which detects an abnormal heart beat and determines whether this abnormal heart beat is amenable to shock therapy.

B. Description of the Prior Art

Defibrillators are devices which apply electric therapy to cardiac patients having an abnormally high heart rhythm. Two kinds of defibrillators are presently available: internal defibrillators which are implanted subcutaneously in a patient together with leads extending through the veins into the cardiac chambers, and external defibrillators which are attached (usually temporarily) to the patient. External defibrillators are used in most instances in case of an emergency, for example, when a patient has either suffered cardiac arrest or where a cardiac arrest is imminent. Typically therefore external defibrillators are manual devices which must be operated by a physician or other trained personal. Internal or implantable defibrillators (and cardioverters) are implanted as a permanent solution for patients having specific well defined cardiac deficiencies which cannot be treated successfully by other means. They generally operate in an automatic mode.

However, there are some instances where an external defibrillator would be very advantageous which could be operated in both automatic and manual modes. For example, presently, it is well known that after a cardiac episode, such as a sudden cardiac arrest, many patients frequently suffer a second episode of similar nature. Therefore, cardiac patients are kept in a hospital under observation. While in the hospital, the patient is attached to a monitor which indicates the patient's heart rate, temperature, respiration rate and other vital signs. Many monitors are provided with an alarm function which is activated when these vital signs fall outside a nominal range. The monitor then generates an audible and visual signal at the bed side of the patient and/or at the remote location such as a nurse station. However, if a cardiac episode does occur, the attending staff has to examine the patient to determine that the patient needs electrical therapy, call the code team, bring a defibrillator to the patient, reconfirm the patient still needs electrical therapy, and then set up and use the defibrillator. All these steps are inherently time-consuming.

Some attempt has been made to overcome some of these problems. For example, some external defibrillators are available which can verify that a patient is suffering from ventricular fibrillation VF and prompt an attendant to activate the defibrillator for the delivery of therapy. However, the algorithms used by these defibrillators to detect VF are very limited. For example, some of defibrillators utilize an algorithm in which the electrocardiogram ECG can be verified only while the patient is unconscious, has no pulse and does not breath. Obviously, these algorithms are not satisfactory since it is important to detect when those conditions happen and apply therapy as soon as those conditions are detected.

Commonly-owned U.S. Pat. No. 5,474,574 discloses an external defibrillator. Commonly-owned U.S. Pat. No. 4,576,170 discloses an external defibrillator that can be worn by a patient.

OBJECTIVES AND SUMMARY OF THE INVENTION

An objective of the present invention is to provide an automatic external cardioverter defibrillator which is capable of recognizing and differentiating between ventricular and supraventricular tachyarrhythmia.

A further objective is to provide a defibrillator capable of performing both amplitude and frequency analyses by using a modulation domain function on a patient's ECG and to use the results of these analyses to categorize or recognize the current condition of the patient.

Yet another objective is to provide an external defibrillator with several modes of operation, including at least one mode in which the modulation domain function is disabled.

Other objectives and advantages of the invention will become apparent from the following description of the invention.

This invention pertains to an automatic external cardioverter defibrillator which can be used to apply anti-tachyarrhythmia therapy in any one of three modes of operation: an automatic mode, an advisory mode, and a manual mode. In the automatic mode, the defibrillator is attached to a patient with risk of sudden cardiac arrest, continuously monitors the patient, automatically detects a cardiac condition for which electrical shocks are indicated (referred herein after as "shockable tachyarrhythmias") and automatically administers therapy in accordance with a set of parameters without any human intervention. These parameters are determined or set during an initialization process during which the defibrillator is customized by a clinician to match the characteristics and needs of a particular patient.

The therapy delivered by the defibrillator generally includes a series of a predetermined number of defibrillation shocks, delivered at intervals and energy levels that may be individually programmed. At the time a shock is delivered, the defibrillator reconfirm the patient is still in a shockable condition. If the patient is converted, either spontaneously or by other means, to a non-shockable condition, the defibrillator internally disarm the charge and does not deliver the shock to the patient. This feature is called non-committed feature. The defibrillator described in this invention is a non-committed device. Preferably, each shock is synchronized to an intrinsic pulse (R wave), if such a pulse is found within a 2.5 second period. If no intrinsic pulse is detected within that period, then a shock is applied asynchronously. Either defibrillation shocks and anti-tachycardiac therapy may be applied. This automatic synchronization feature eliminates the need for a synchronization button and the need for the operator to select the button position.

After each shock, the defibrillator reexamines patient's cardiac condition. If the shock condition still exists, the defibrillator steps up to the next shock. These successive shocks may have the same or an increased energy level. This process continues until either the patient is converted to a non-shockable condition, or the therapy sequence is completed whichever happens earlier.

However, if the patient is converted to a non-shockable condition after a shock, the programmed therapy sequence resets when the defibrillator detects a period, e.g. 60 seconds, of non-shockable condition. The defibrillator considers the current shockable episode is converted and completed. If defibrillator detects a new shockable episode later, the defibrillator delivers the therapy from the first shock.

The operation of the defibrillator in the advisory mode is very similar to the automatic mode in that the same algorithm is used to detect shockable rhythms. However, in this mode, a visual and aural indication is provided when the defibrillator is ready to apply shocks. The attendant can then activate shock button(s) to deliver the shock. Successive shocks may be delivered in the same manner. These successive shocks may have the same or an increased energy level. The application of the successive shocks continues under the direction of the attendant until either the shockable condition is terminated or the therapy sequence is completed, whichever happens earlier.

If an attendant does not activate the pushbuttons within a preset time period after the defibrillator indicates its readiness (e.g., within about 35 seconds), the defibrillator resets itself and generates a message for the attendant that the therapy has been terminated.

The defibrillation shocks are generated by the defibrillator from a energy storage component, e.g. a capacitor, charged to a predetermined energy level. As part of all resetting sequences, the defibrillator dissipates internally the charge on this capacitor.

In the manual mode, the defibrillator performs functions similar to other manual defibrillators. The attendant, in this mode, can visually monitor the status of the patient, can initiate the charging of the energy storage component to one of several energy levels and can discharge the capacitor through the electrodes using command pushbutton(s) provided for this purpose. However, if after the charging of the capacitor, the attendant fails to request a shock within a preset time period, the defibrillator may discharge the capacitor internally.

In order to perform the functions described above efficiently and to provide historical information to the attendant, the defibrillator includes an ECG detector used to detect intrinsic ECG signals from the patient, a tachyarrhythmia detector which may be software-based and which is used to identify a shockable rhythm, as well as a recorder for data logging and a printer that can be used to print data automatically or manually. The defibrillator is associated with electrodes assembly comprising a pair of defibrillator pads (required) and sensing electrode pairs (optional). The ECG detector can selectively use signals either from the sensing electrode pairs or even the defibrillator pads.

The defibrillator can be run from a standard AC line and/or a set of built in stand-by batteries.

Another aspect of the subject device pertains to the method and elements used to detect and confirm the current cardiac rate or rhythm of the patient. Unlike the straightforward average which contains errors from both over-sensing and under-sensing of the QRS's, the concept or the purpose of this method is to reduce effect on the detected heart rate from over-sensing and under-sensing of the QRS's. This invention includes the concept and an implementation of this method. Briefly, the periods between consecutive QRS's obtained from the patient are detected and averaged. The absolute difference between this average and the duration of each of these periods is calculated and the period corresponding to the largest difference is discarded. A new average is then calculated using the remaining periods, the differences are again calculated and the period with the largest difference is again discarded. The current cardiac rate is then determined using the average duration of the remaining periods N−2 where N is the total number of periods in the calculation. In this manner, periods which may have been erroneously sensed due to over- or missed due to under-sensing are eliminated.

Another aspect of the invention pertains to a method and system for detecting tachyarrhythmias and separating such events from other events such as supra-ventricular tachycardia SVT. The defibrillator analyses both the frequency and the magnitude of the sensed ECG signals using a modulation domain function or MDF mode. This approach is superior to other known analysis methods such as FFT and amplitude density analyses (such as PDF). Briefly in accordance with this invention, events with wide complexes are assigned a higher MDF value then period with narrower ECG complexes, for rates within a predetermined range. If the MDF value meets certain predetermined criteria, the cardiac rhythm is shockable and, accordingly, appropriate therapy is applied.

The MDF mode is selected to reduce the probability of delivering therapy to SVT's that may be within the preselected rhythm range, without compromising the sensitivity of the ventricular tachyarrhythnia therapy. As the cardiac rate increases the probability of an SVT event is reduced and the probability that a shock is required increases. The MDF is designed to differentiate between the two (ventricular tachycardia VT and SVT) conditions in the overlapping cardiac rate range.

The MDF feature or mode can be deactivated, in which case, a standard detection rate is applied.

If the MDF mode is on, the MDF threshold rate for which the MDF is operative is programmed by the attendant. In this mode, for cardiac rates above the detection rate and below the MDF rate, the MDF value must satisfy a pre-related criteria before shock is applied. At rates above the MDF rate, the MDF value is ignored and therapy is applied as required.

DETAILED DESCRIPTION OF THE PREFERRED EMBODIMENT

Figure 1:
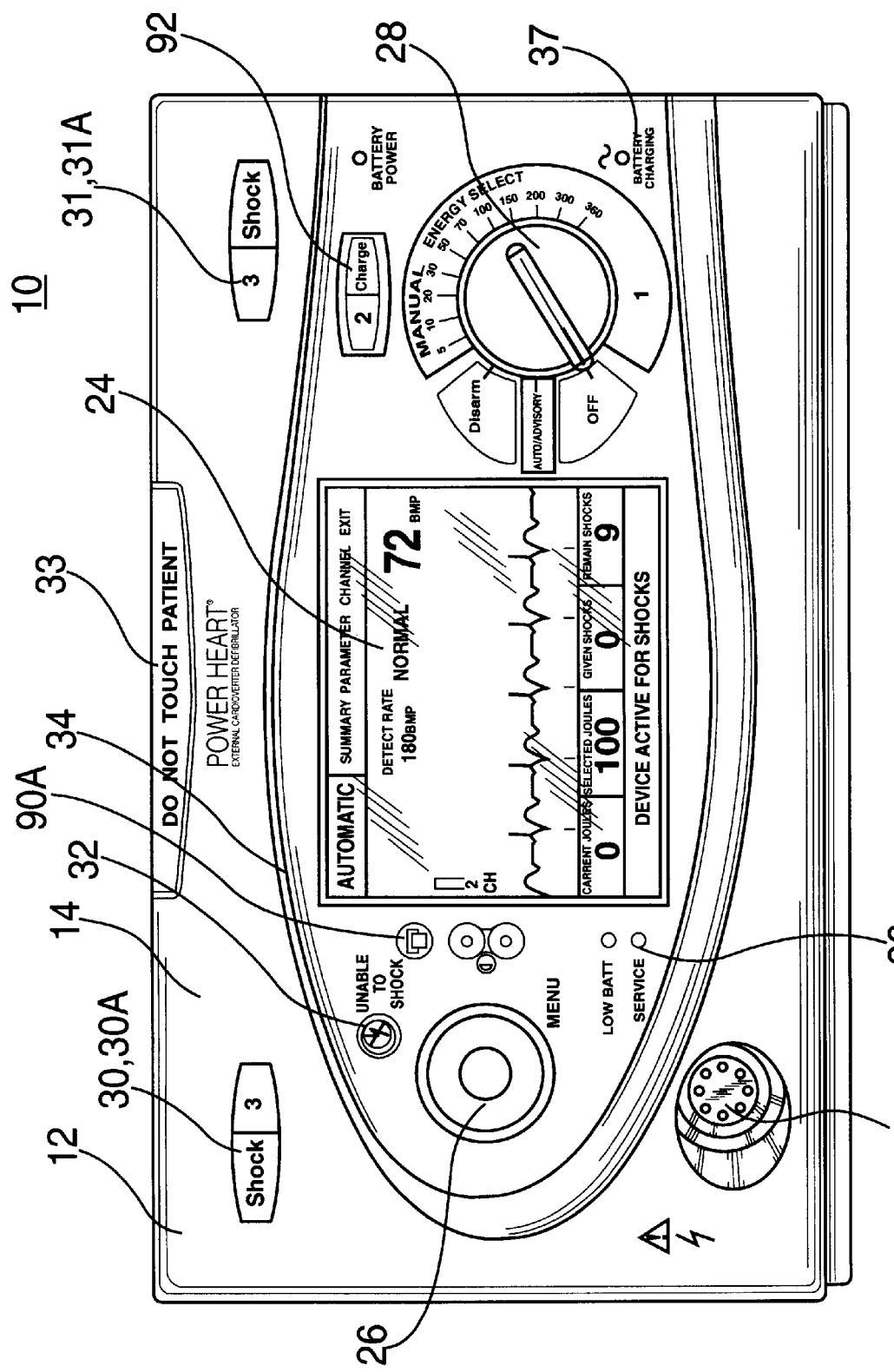
FIG. 1 shows a front view of an automatic external cardioverter defibrillator constructed in accordance with the subject invention.
Figure 2:
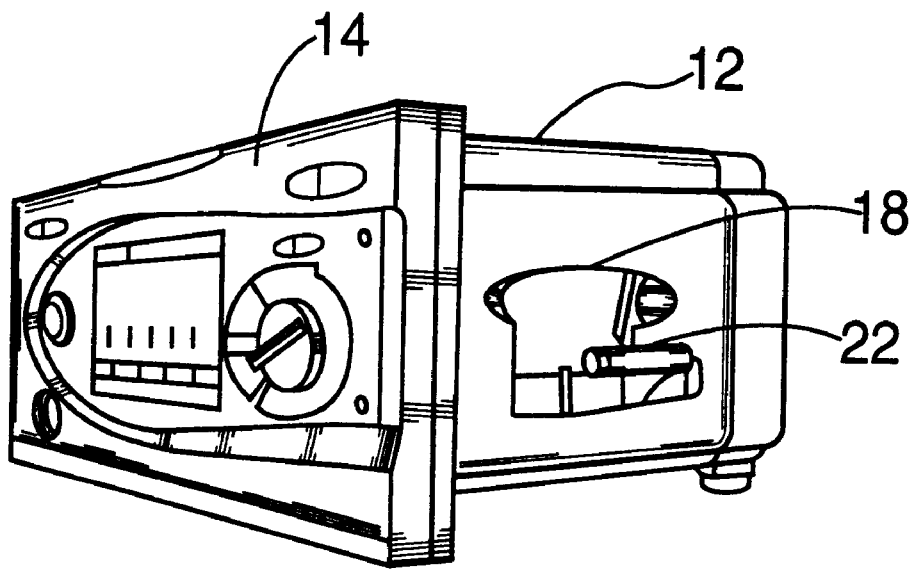
FIGS. 2 and 3 show an orthogonal view of the defibrillator of FIG. 1 with details of the printer on the side of the housing.
Figure 3:
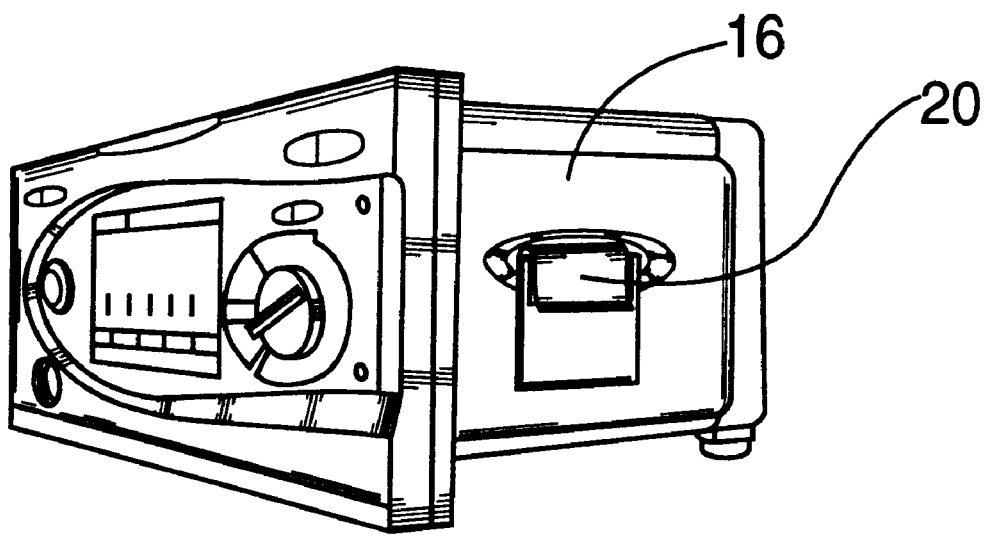

FIG. 1 shows a defibrillator 10 having a housing 12 with a front face 14 on which a plurality of controls and indicating elements are provided, as described in more detail below. The defibrillator further includes electrode assembly shown in FIG. 4 and described in detail below. As seen in FIGS. 2 and 3, one side 16 of the housing 12 is provided with a cavity 18. A printer (not shown) is mounted in cavity 18. A roll of paper 20 is mounted on shaft 22 in a manner which allows the printer to print alphanumeric characters and graphics on paper 20.

The housing 12 can be positioned on a rack, or other support means so that it can be disposed adjacent to the patient.

Referring back to FIG. 1, a screen display 24 is mounted on the front face 14 so that it is clearly visible. The display is used to provide information to the clinician related to the operation of the defibrillator 10, the status of the patient, etc. Disposed around the display 24, there are other indicator and control elements, such as the menu selection knob 26, charge button 92, selector knob 28, shock buttons 30, 31 with built-in lights 30A, 31A respectively, and indicator lights 32, 34 and 36.

The menu selection control knob 26 is used in combination with the display 24 to select various operational parameters or for the defibrillator 10.

The knob 28 has several positions defining modes of operation, such as: Off, Auto/advisory, Disarm and energy selection in Manual mode. In the Off position, the defibrillator is deactivated. In the auto/advisory position, the defibrillator monitors the patient and can apply shocks using a preselected therapy. In the disarm position, an internal capacitor (not shown) is discharged to ensure that the defibrillator does not apply a shock accidentally. Finally, in an energy selection position, the defibrillator may be used to apply a shock to a patient at the selected energy level.

Figure 4:
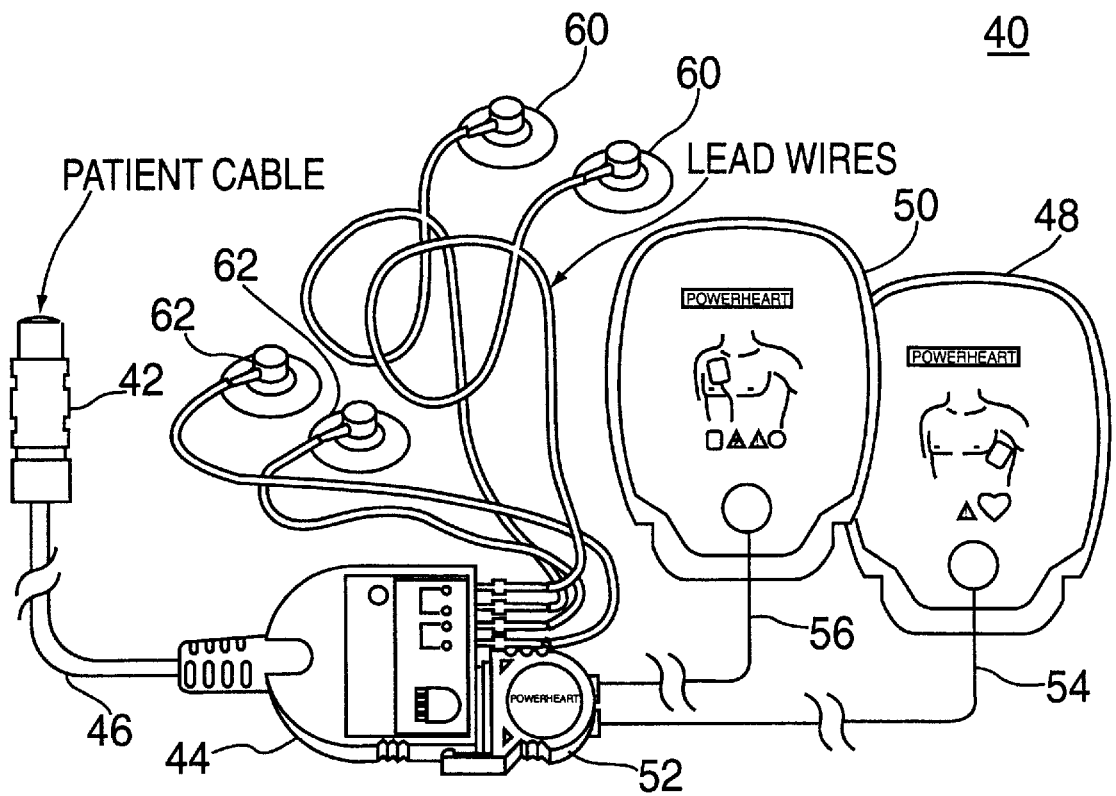
FIG. 4 shows the defibrillation and sensing electrodes used with the defibrillator of FIG. 1.

A socket 38 is provided for mating the housing 12 to the electrode assembly of FIG. 4. Near the top of the face 14, the housing 12 is provided with an additional illuminated indicator 33.

FIG. 4 shows details of the electrode assembly 40. The assembly 40 includes a first plug 42 constructed and arranged to mate with the jack 38 (FIG. 1), a connector 44 and a cable 46 extending between the plug 42 and the connector 44.

The assembly 40 further includes a pair of defibrillator pads 48 and 50 coupled to the connector 44 by an adapter 52, and two leads 54, 56 connected respectively to sensor electrode pairs 60 and 62.

Figure 5:
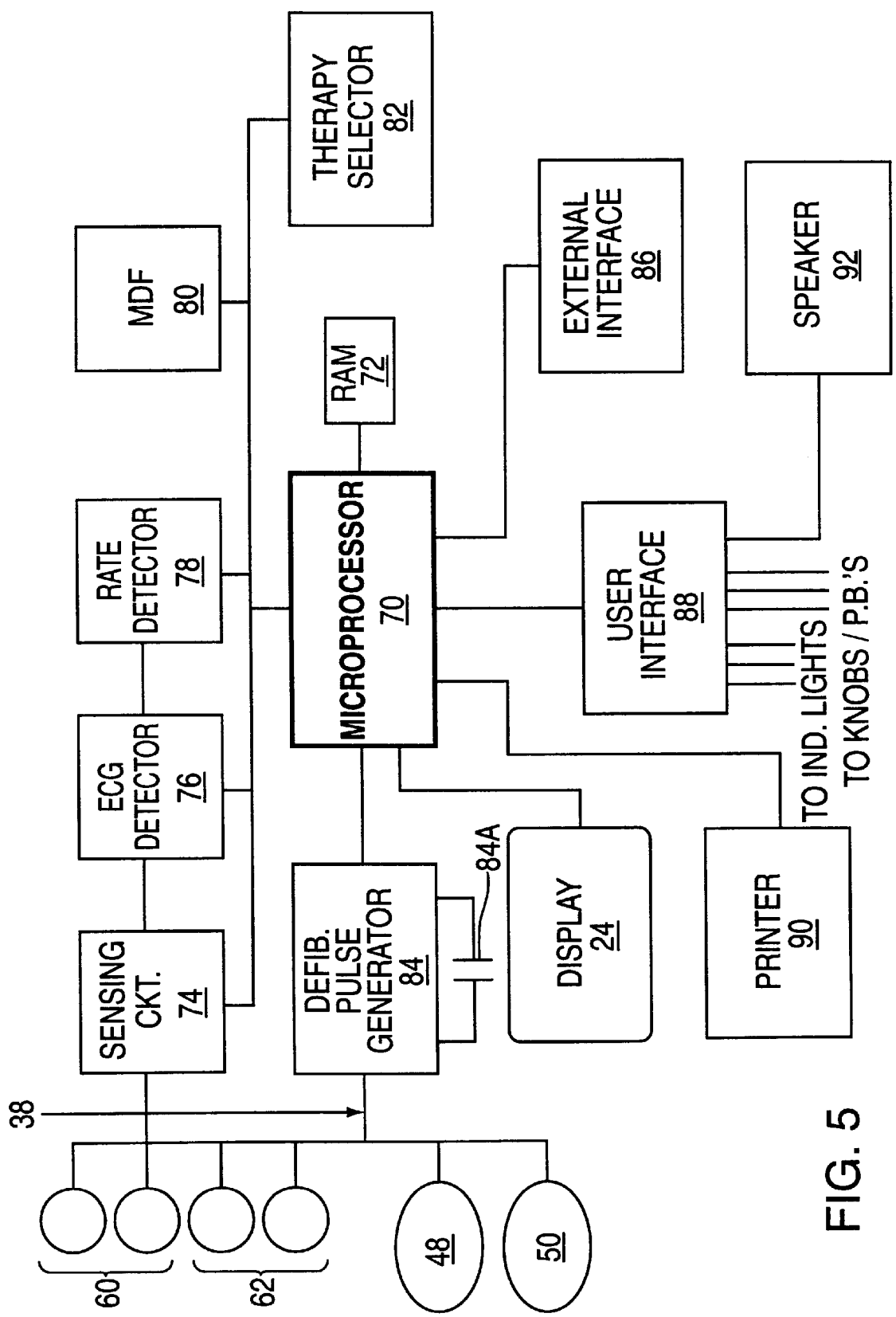
FIG. 5 shows a block diagram of the circuitry for the defibrillator of FIG. 1.

The defibrillator 10 also includes electronic circuitry disposed in housing 12 and used to operate the defibrillator and to generate the required electrical therapy. Referring to FIG. 5, the circuitry includes a microprocessor 70 which is associated with a memory 72 for storing programs and data logging information. The defibrillator further includes a sensing circuit 74, an ECG detecting circuit 76, a rate detector circuit 78, an MDF circuit 80, a therapy selector circuit 82, a defibrillator shock generator 84, an external interface 86, and a user interface 88. The microprocessor 70 receives commands from an attendant and other control signals through the various knobs, and push buttons shown in FIG. 1 via the analog interface 88. The microprocessor also activates various visual indicators and a speaker (not shown) through the same interface 88. The circuits shown in FIG. 5 can be implemented by software in RAM 72 however are shown as discrete circuits for the sake of clarity. Energy for the shocks is derived from a capacitor 84A associated with the generator 84.

As can be seen in FIG. 5, the electrode pairs 60, 62 and pads 48, 50 are connected through the jack 38 to a sensing circuit 74. This circuit 74 senses the intrinsic signals detected from the heart of the patient through the electrodes or defibrillation pads, filters the same, converts them into digital signals at a sampling rate of, for example, 512 samples per second. Of course the filtering can be performed on the digital signals as well. The circuit 72 further includes an impedance measuring element (not shown) which measures the impedance of between the pads. This impedance is provided to the microprocessor 70 so that the latter can determine if the pads and sensors are properly attached to the patient. The sensing circuit also detects if the sensing electrodes are connected properly.

The sampled digital signals from circuit 74 are fed to the microprocessor 70. The ECG detector circuit 76 and the rate detector circuit 78. The ECG detector 76 detects the ECG complex of the patient. The rate detector circuit 78 detects the current cardiac rate of the patient.

The microprocessor 70 analyzes the signals received from circuits 74, 76 and 78 and operates the other elements of defibrillator in accordance with these signals as discussed in more details below. In addition, the microprocessor 70 also sends information requested by an attendant to printer 90 when a pushbutton 90A (FIG. 1) is activated. In some cases, the microprocessor 70 activates the printer 90 automatically, for example, to display an ECG during defibrillation therapy.

The microprocessor can also exchange information with other devices or to display a current ECG through an external interface 86.

Figure 7:
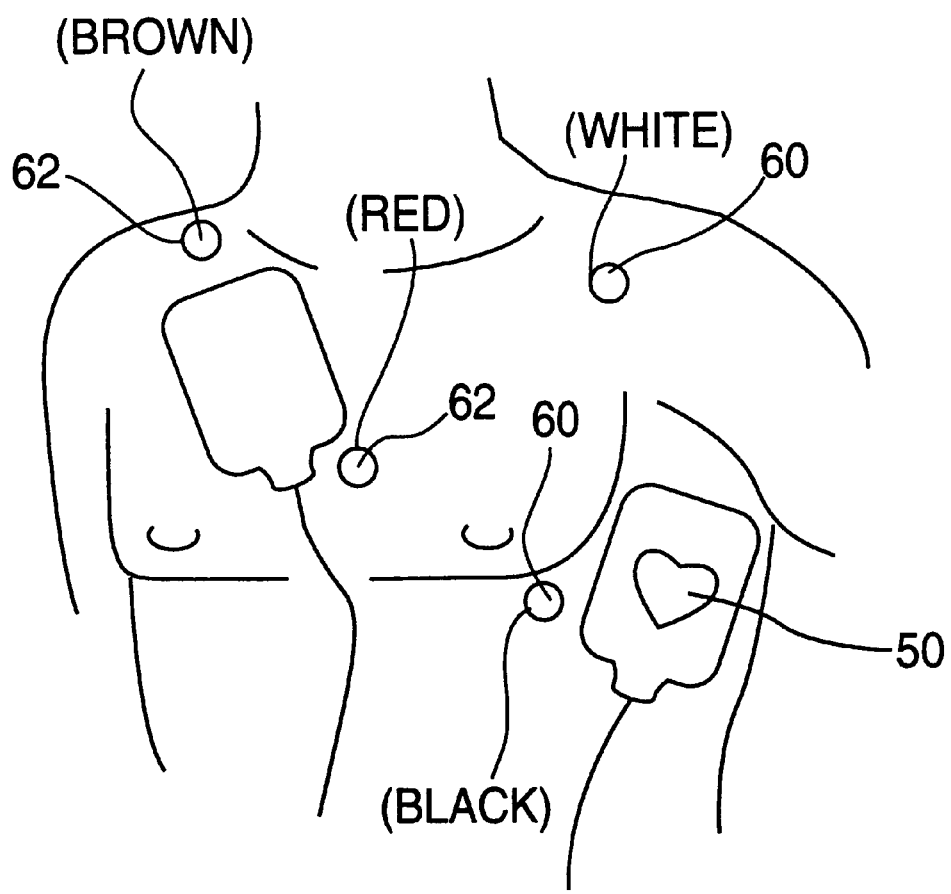
FIG. 7 shows diagrammatically the placement of the electrodes of FIG. 4 on a patient.

Before turning on the defibrillator 10, the pads 48, 50 and electrodes 60, 62 are positioned on the patient. FIG. 7 shows one possible positioning for these elements.

Figure 6:
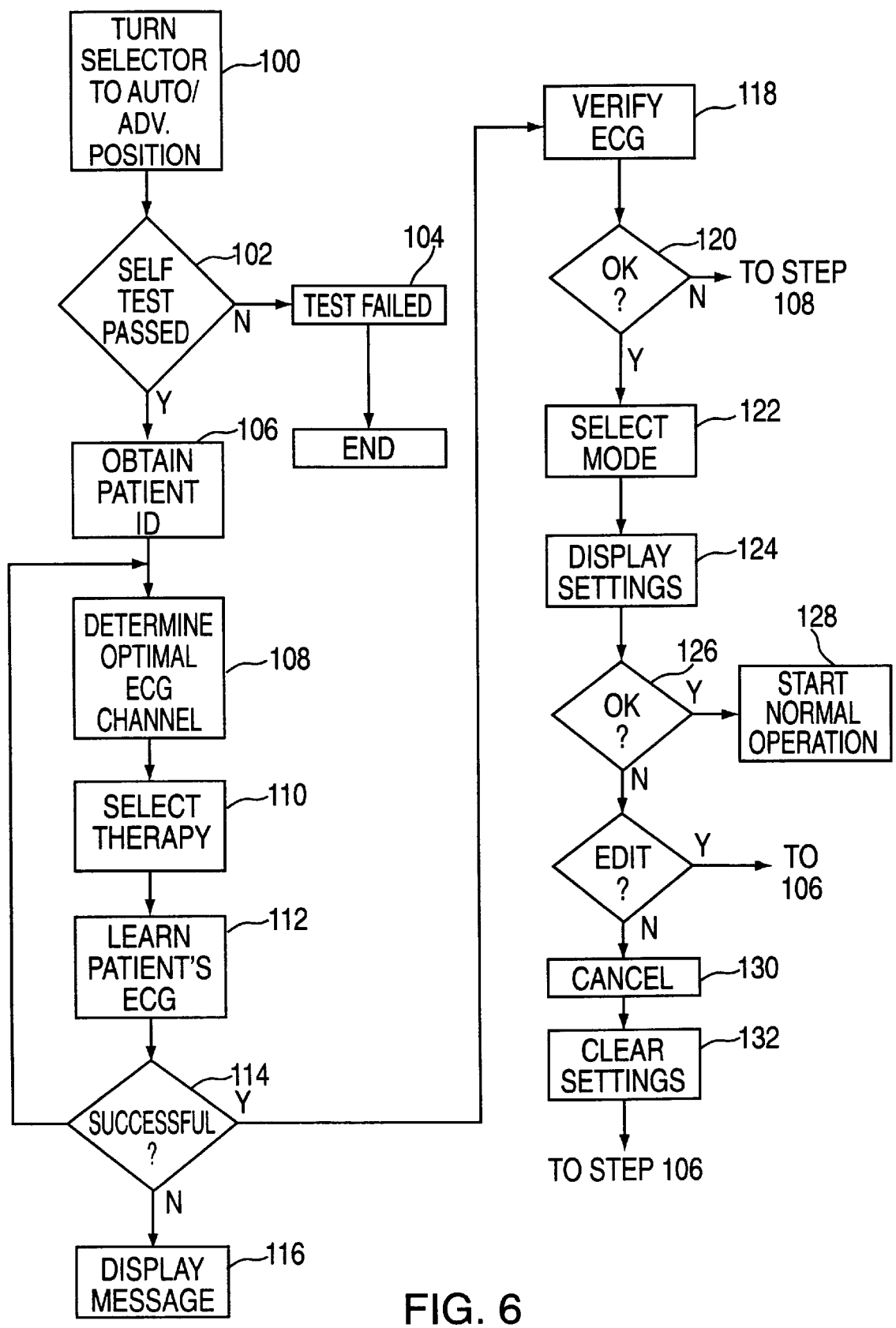
FIG. 6 shows a flow chart illustrating the steps required to initialize the defibrillator of FIG. 1.
Figure 9:
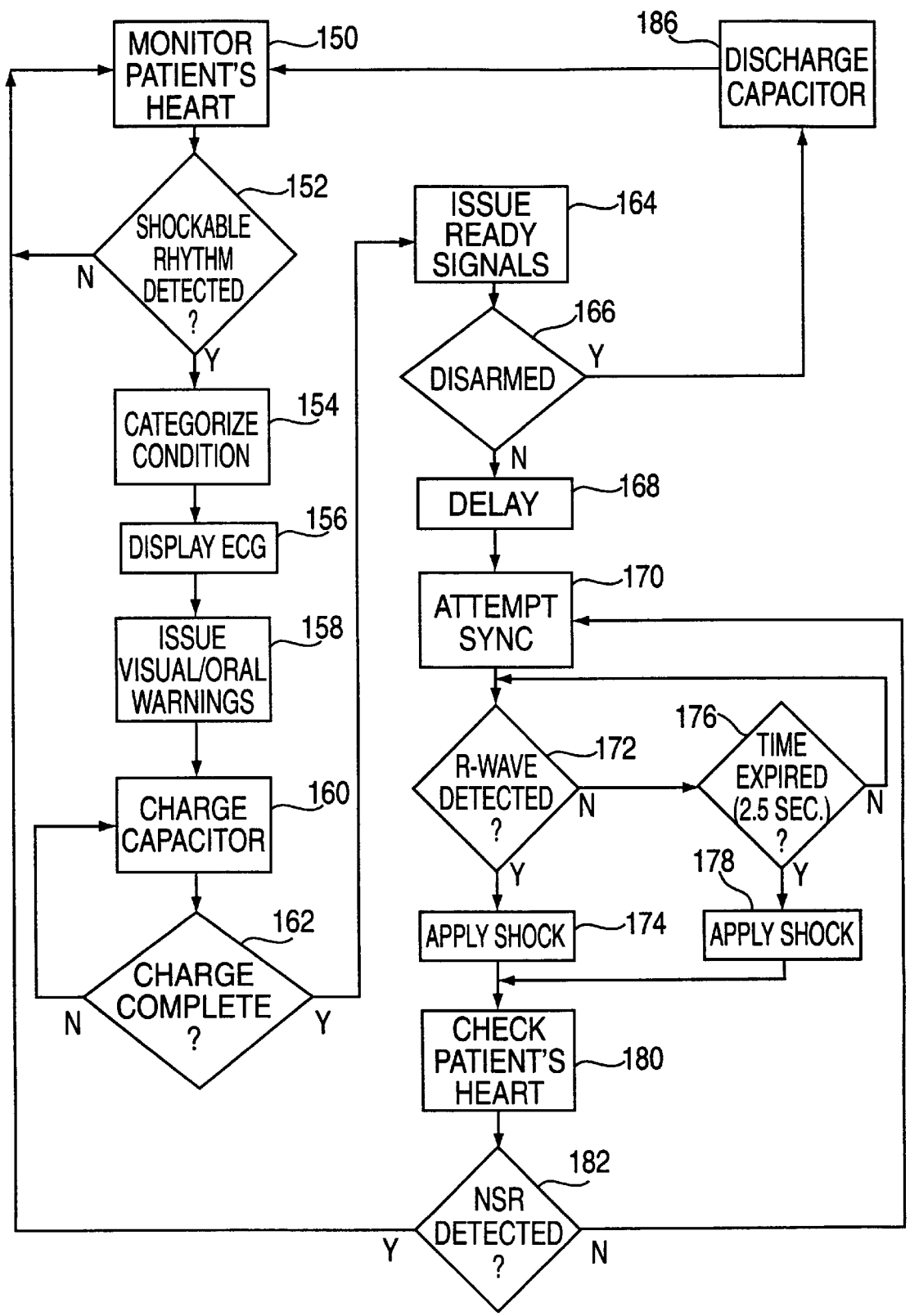
FIG. 9 shows a flow chart for the operation of the defibrillator of FIG. 1.

The operation of the defibrillator 10 and its microprocessor 70 is now described in conjunction with the flow charts of FIGS. 6 and 9. Before the defibrillator 10 can be operated, it must be initialized. This stage of initialization may be performed whenever the defibrillator 10 is set up for a particular patient. In one embodiment of the invention, the defibrillator 10 can be set up for only one patient at a time. In another embodiment, the defibrillator may be set up to provide therapy selectively to one of several patients, in which case, operational parameters unique for each patient are stored in its memory 88.

The first step in the initialization stage, step 100, the defibrillator 10 is turned on. This may be performed, for example, by turning the selector knob 28 to the auto/advisory position.

Once the defibrillator 10 is activated, it goes into a self-test mode (step 102) during which various internal functions and components are tested. During this step 102, the indicator light 32 illuminates to indicate that the defibrillator is currently unable to apply shocks and various sounds are emitted from the speaker (not shown) as well.

If the self-test fails in step 102, then in step 104, an error message is shown on display 24 and the initiation process is aborted.

If the self-test passes, then in the next step 106, the ID of the patient to be treated is obtained. For example, instructions may be shown on display 24 requesting the name and/or a unique number for the patient. The patient ID can be entered by manipulating the knob 26 or by using a keyboard (not shown). The patient ID can be optional.

Next, in step 108, the ECG signals are analyzed to determine the best channel for the ECG acquisition. More particularly, the two pairs of sensing electrodes and the pads (which are also used in this instances as a sensing electrode pair) define three separate detection channels. The detection channel is selectable by an attendant.

Figure 8:
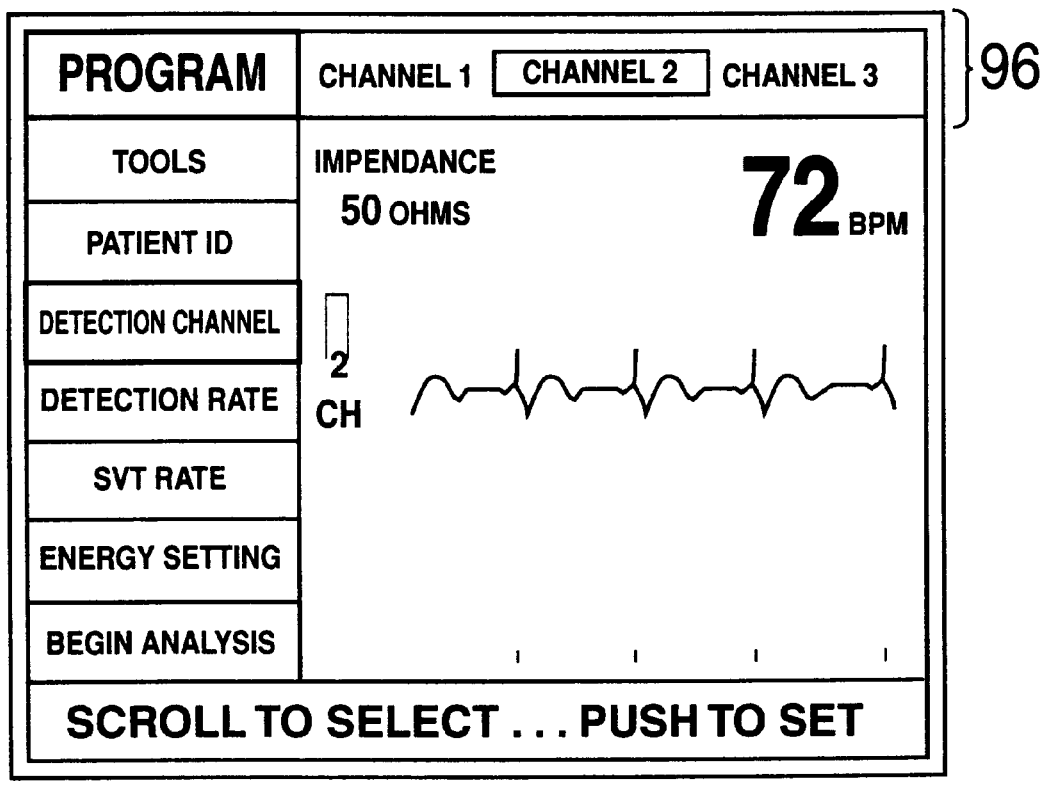
FIG. 8 shows a view of the display while an ECG is acquired during the initialization process of step 6.

Referring to FIG. 8, a portion 96 of display 24 identifies three detecting channels as channels 1, 2 and 3 respectively. In step 108, each of these channels is selected by manipulating knob 26. As each channel is selected, the ECG sensed through the corresponding pair of electrodes, the electrode pair impedance of the defibrillation pads, and current heart beat sensed through the electrodes is shown on the display 24. For example, in FIG. 8, an ECG is shown as it is sensed from channel 2 (which may correspond to electrode pair 60), with an electrode impedance of 50 ohms and a heart rate of 72 beats. These measurements are derived by the microprocessor 70 from the signals sensed through the sensing electrode pairs, the sensing circuit 74, the ECG detection circuit 76, and rate detection 78. The attendant setting up the defibrillator examines the ECG and other parameters for each channel and based on his observations and experience he then selects the best or optimal channel by manipulating knob 26.

Next, in step 110, the parameters for a particular therapy are selected by the attendant, including a cardiac rate Rmin. The range of Rmin is about 120–240 BPM. Another parameter set during step 110 is the rate Rmdf. Generally, the rate Rmdf is higher than Rmin.

The defibrillation therapy delivered by defibrillator 10 consists of one or more shocks. More particularly, the defibrillator 10 can be set to deliver a number of sequential shocks, for example, one to nine; each having an energy level in the range of 5 to 360 joules. The interval or delay between shocks can also be set from 10 to 600 seconds in either 5 or 10 second increments. These parameters are all selected in step 110. Moreover, if multiple shocks are used, the energy level and or delay of each shock may be constant or can be separately programmed to predetermined levels.

After the operational parameters of the defibrillator 10 have been set (or programmed) in step 110, the defibrillator proceeds to learn to recognize the ECG of the patient in step 112. During this step, the microprocessor 70 monitors the signals sensed on the channel designated in step 108 for a predetermined time period (for example, 20 seconds). In step 114, a test is performed to determine if the ECG signal recognition was successful. For example, during this period the heart rate is determined from the ECG by determining the time interval between successive R-waves, and compared to the Rmin. In addition the amplitude of the ECG signal is compared to a threshold value (such as 0.7 mv). If the heart rate is found to be below the rate Rmin and the amplitude is found to exceed the threshold then the recognition step is successful. If the recognition process is not successful, then in step 116, a message is displayed to indicate failure and the process is aborted. In step 116 suggestions may also be made to the attendant which may cure the problem. For example, the attendant may be asked to reposition the electrode pairs, and/or select a different sensing channel.

If the learning process is found to be successful, then in step 118, the ECG is shown on the display 24 together with the pertinent parameters and the attendant is requested to verify these parameters. In step 120, the attendant is given the choice of accepting the ECG or to reject it. If the attendant rejects the ECG, the process is aborted. If the attendant accepts the ECG, then in step 122, the attendant is asked to select a mode of operation (i.e., automatic or advisory). In step 124, the choices made during the initialization process are displayed to the attendant. The attendant can request that the selected parameters and mode of operation be printed out during this step.

In step 126, the attendant is given the choice of accepting the parameters as they were set in steps 106–122. If the parameters are accepted, then in step 128, the initialization process is completed, the programmed parameters and other information can be printed automatically, and the operation starts its normal operation mode.

If in step 126, the attendant does not approve the parameters but instead selects to edit them then the process goes back to step 106.

If the attendant decides to cancel the selected parameters (step 130), the process is aborted.

Once the defibrillator 10 has been properly initialized, it is ready for operation. As described above, the mode of operation of the defibrillator 10 is determined by position of the selector switch 28. If this switch is in the auto/advisory position, and it has been previously set to the automatic mode, then it operates as described in the flow chart of FIG. 9. Starting with step 150, the defibrillator first monitors the condition of the patient's heart. During this time, the display 24 is used to show the following information: the mode of operation (in this case AUTOMATIC), the current ECG, the current heart rate Rcur and the selected Rmin.

Figure 9A:
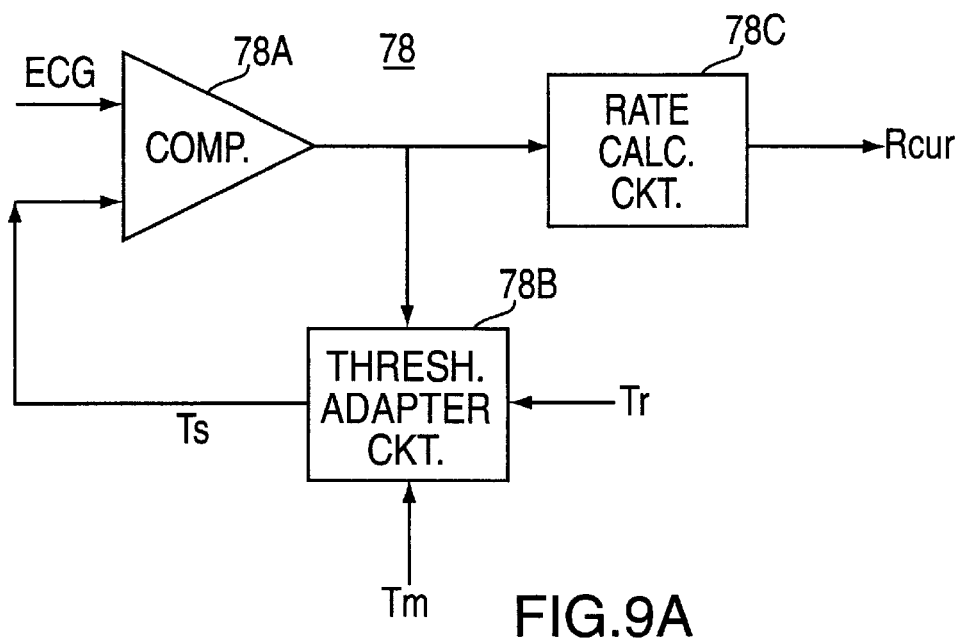
FIG. 9A shows details of a rate detecting circuit for the defibrillator of FIGS. 1–5.
Figure 9B:
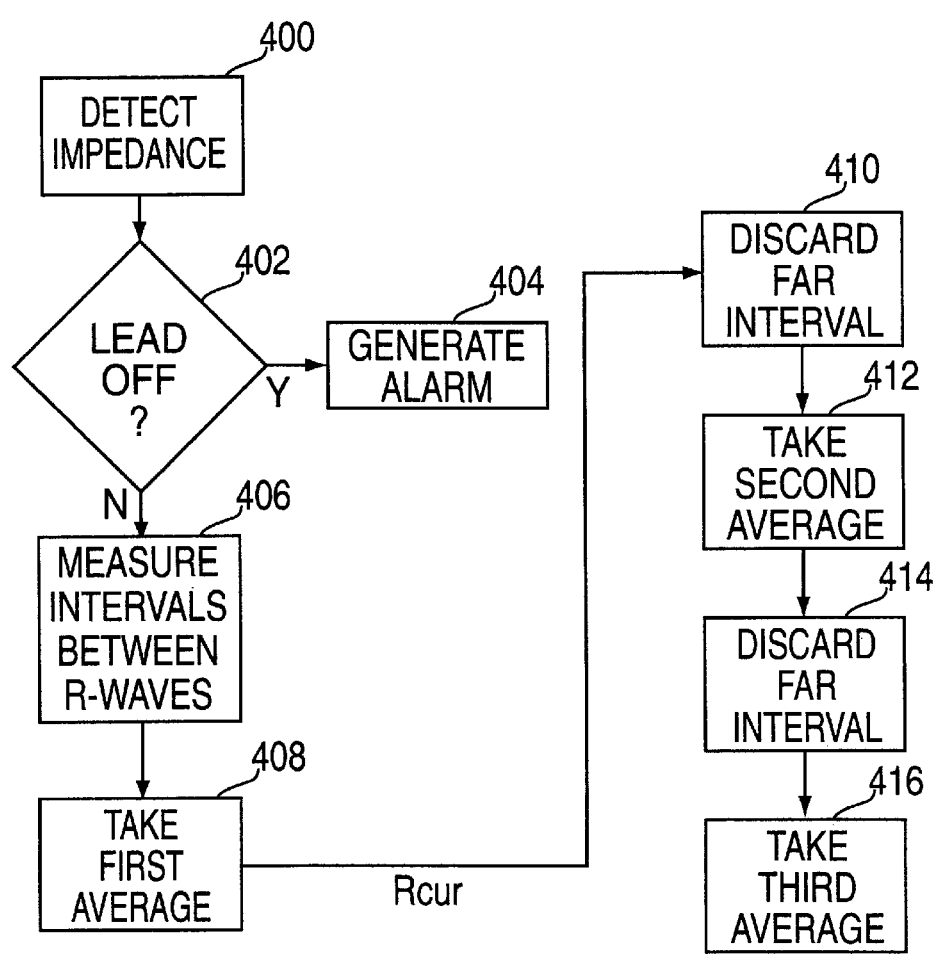
FIG. 9B shows a flow chart for the operation of the circuit of FIG. 9A.

The current heart Rcur is determined using the circuit 78 as shown in FIGS. 9A and 9B. The circuit 78 includes a comparator 78A, a threshold selector circuit 78B and a rate calculator circuit 78C. The comparator 78A and the threshold selector circuit 78B cooperate to detect the intrinsic ventricular rate in an adaptive manner. That is, prior to the acquisition of any signals, the circuit 78B selects a low threshold level Tr which may in the order of 0.2 milli-volts. Once a sensed signal exceeding this level is detected by comparator 78A, the signal is identified as a potential R-wave. Thereafter. for a predetermined time period for all future incoming signals, the threshold level is increased slightly until a maximum threshold level Tm is reached. In this manner, a multiple digital signal processing method is used to detect the intrinsic cardiac signals using an adaptive threshold.

Next, the signals detected by comparator 78A are fed to a rate calculator circuit 78C. This circuit also receives a signal indicative of whether the electrodes currently being used to detect the ECG complex are connected properly. This circuit 78C measures the interval between consecutive signals and generates the corresponding ventricular rate, using a special averaging technique. This technique from comparable 78A has been selected to eliminate the adverse effects of over-sensing and under-sensing the cardiac signals. More particularly, referring to FIG. 9B in step 400, the impedance signal is detected and analyzed. In step 402, a test is performed to determine if this signal is abnormally high, indicating that a lead (or electrode) is off. If a lead is off, then in step 404, an alarm is generated and the rate calculation process is terminated. As part of step 404, a message is shown on display 24 with instructions to the attendant for correcting the problem.

If, in step 402, it is determined that the electrode impedance is acceptable, then in step 406, N intervals between sequential events from comparator 78A are measured. In step 408, a first average AI1 is taken of the N intervals. In step 410, the absolute difference is determined between the average AI1 and each of the intervals. The interval with the largest difference is discarded.

Next, in step 412, a new average AI2 is generated using the remaining N−1 intervals. In step 414, again, the absolute difference between each of the remaining intervals and the average AI2 is determined and the interval corresponding to the largest difference is discarded. In step 416, an average is taken of the remaining N−2 intervals and this average, or more properly, its inverse, is designated as the current cardiac rate Rcur for the patient's heart. This process (steps 400–416) is repeated for each new electric event (peak or QRS) from the comparator 78A.

Figure 10:
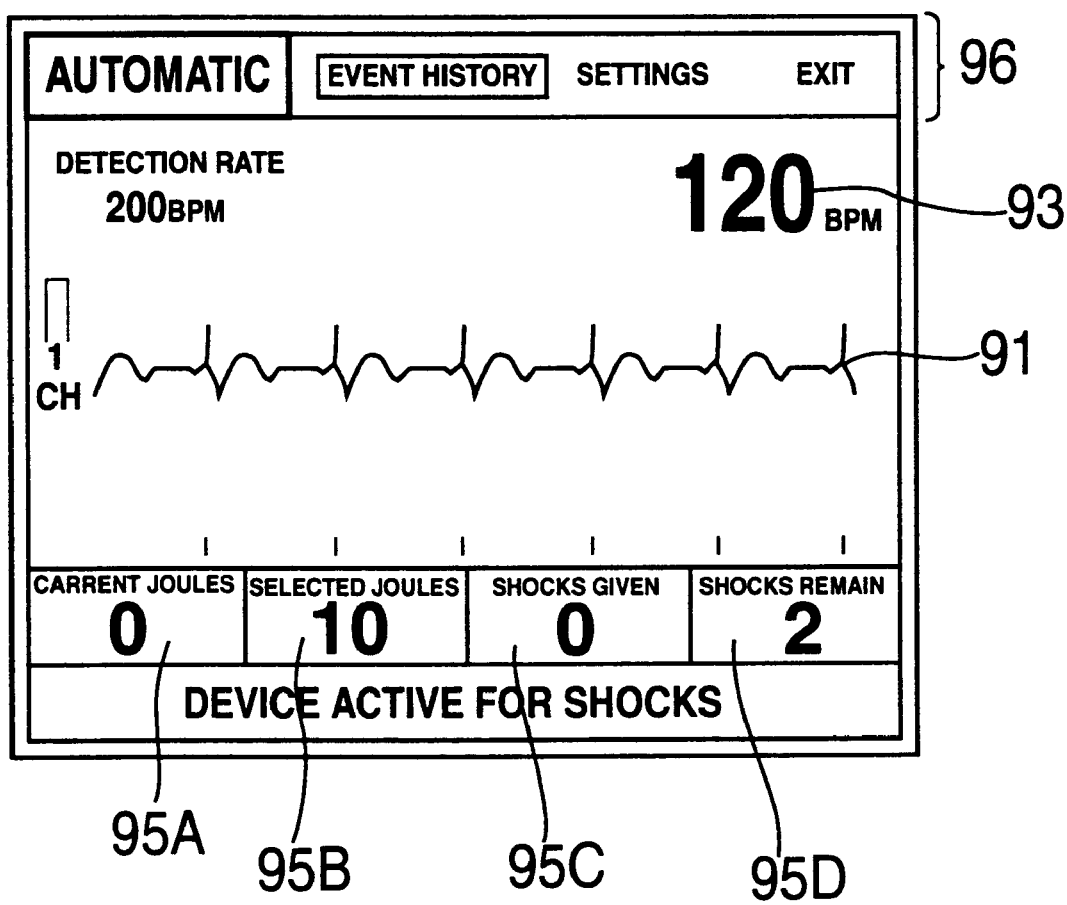
FIG. 10 shows the screen displayed during automatic operation when the defibrillator is ready to apply anti-tachycardia therapy.

Back to FIG. 9, in step 152 at regular intervals, a check is performed to determine if the current rate Rcur (as determined in FIG. 9B) is indicative of a shockable cardiac rhythm is detected. The method of detecting such a shockable rhythm and of determining the corresponding therapy is discussed below, in conjunction with FIG. 14. If a shockable rhythm is detected then in step 154, the arrhythmia is categorized (i.e., as a tachycardia or fibrillation). In step 156, the display 24 is used to show, as indicated in FIG. 10 the current ECG of the patient, at 91, patient's heart rate at 93, and the therapy parameters selected, including the selected energy level, 95A, the number of shocks delivered 95B the total number of shocks programmed 95C and the total number of shocks that remain to be delivered, 95D. Next, in step 158, the defibrillator issues visual and audible warnings to the attendant indicating that the defibrillator is preparing to deliver shocks to the patient and the patient should not be touched. The visual warnings include turning light 33 on (FIG. 1) and the audible signals including voice signals are generated through the speaker (Not shown).

Next, in step 160, the defibrillation pulse generator 84 is activated to start charging its capacitor 84A. As shown in FIG. 10, the display 24 shows during this time the selected or targeted energy level which was set during the initialization mode. The display also shows at 95A the current charge level within the defibrillation pulse generator. As the capacitor within the generator is charged up, this level is increasing, and an audio signal is emitted by speaker (not shown) to indicate this gradual charging process.

In step 162, the charge level of the capacitor is tested to determine if the set energy level has been reached. If this level has not been reached, the charging process continues.

When the selected charging level is complete, the defibrillator 10 prepares to apply shocks. In step 164, the indicator 34 is lit to indicate that the defibrillator 10 is ready to apply therapy.

At any time during the process described so far, an attendant can disable the automatic or advisory mode by moving the knob 28 to the disarm or an energy selection position. In FIG. 9, in step 166, a check is performed to determine if the knob 28 has been shifted to these positions.

If the defibrillator has not been disarmed, then for all shocks, except the first shock of a treatment in step 168, a delay is imposed to conform to the delay programmed between shocks as discussed above. Once the delay is complete in step 170, an attempt is made to synchronize the shock to the ECG. More particularly in step 172, the ECG is analyzed and an attempt is made to detect an R-wave. If an R-wave is detected, then in step 174, a pulse of predetermined duration and energy level is applied to the patient within a predetermined interval, for example 60 milliseconds, after the R-wave.

As step 172 is initiated, a timer (not shown) is also activated. This timer waits for a predetermined time (for example, 2.5 seconds ) for synchronization to be achieved. If no synchronization is achieved in that time period, then in step 178, a shock is applied asynchronously.

The defibrillation shock of step 174, 178 is delivered to the patient by the pads 48, 50 (FIG. 4).

After the delivery of the shock in step 180, the heart rate of the patient is determined. If a non-shockable rhythm is detected (step 182), then no more shocks are applied and the heart monitoring is continued in step 150.

If the shockable rhythm continues, then the process of steps 152–180 is repeated thereby delivering the next level of predetermined therapy.

This process continues until all the predetermined number of shocks are delivered, the system returns to step 150 and continues monitoring the patient.

Preferably, after the predetermined number of shocks is delivered, the heart is monitored in step 150 but no other steps are taken even if a shockable rhythm is detected in step 152 unless the therapy sequence resets after a predetermined period of non-shockable has been detected or the defibrillator has been reset.

If the process described above is halted at any time, for example, by turning knob 28 to the disarm or manual position as set forth above in step 166, then the capacitor 84A associated with the defibrillation pulse generator 84 is discharged internally.

In the above description, it was assumed that a ventricular tachyarrhythmia has been detected in step 154. The process may be modified to suit other types of arrhythmias as well. For example, if a fine fibrillation is detected, the steps 170, 172 are omitted since no synchronization may be achieved.

In the automatic mode, when the peak to peak amplitude of ECG signal is greater than a threshold, e.g. 0.2 milli-volts, to ensure a shock is delivered to a shockable condition, the last intervals immediately before the shock is delivered need to be less than the shockable interval corresponding to the Rmin. In this particular application, two intervals immediately prior to the shock are required to be less than the shockable interval.

Figure 11:
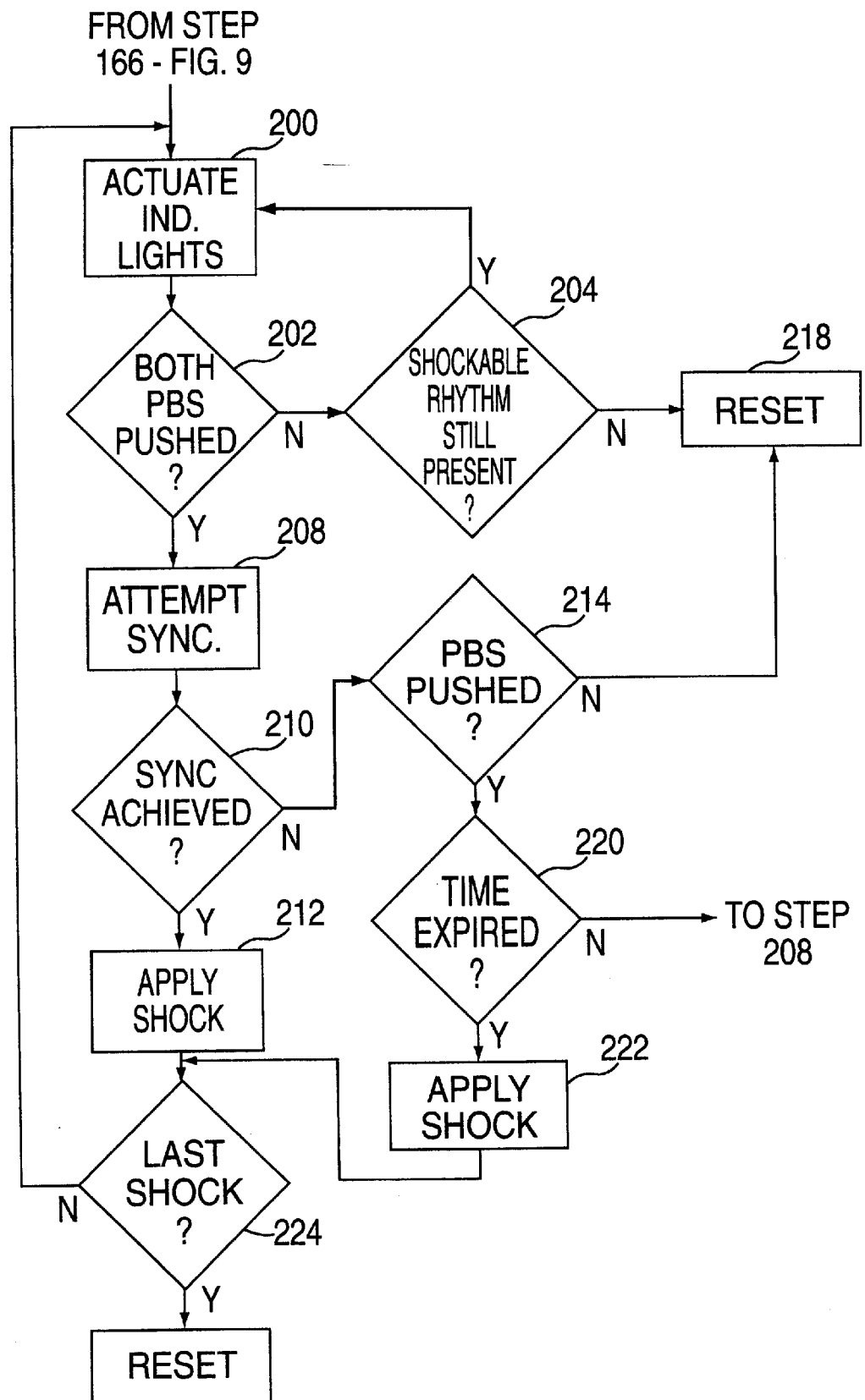
FIG. 11 shows a flow chart illustrating the operation of the device in the advisory mode.

As previously mentioned, one of the operational modes of the defibrillator 10 is an advisory mode. This mode is now described in conjunction with FIG. 11. In this mode the defibrillator performs the same functions that are performed in the automatic mode starting from step 150 through step 166 (FIG. 9). However, after step 166, instead proceeding with the delivery of shock therapy, the lights 30A, 31A associated with pushbuttons 30 and 31 respectively are activated and indicating to an attendant that the defibrillator is ready to apply a shock. The attendant can then elect to apply a shock by depressing pushbuttons 30, 31 simultaneously. A check is performed in step 202 to determine if the pushbuttons have been depressed. If they have not been depressed, then in step 204, a check is performed to determine if the shockable rhythm is still present. If the rhythm is still present, then the lights 30A and 31A remain activated in step 200 and the system continues to wait for the activation of buttons 30, 31. If, in step 204, it is found that a shockable rhythm is no longer present, then the system is reset in step 218.

If the buttons 30, 31 are found activated in step 202, then in step 208, an attempt is made to synchronize with the R wave. In step 210, a check is performed to determine if synchronization was achieved. If synchronization is achieved then a shock is applied in step 212. In step 224, a check is performed to determine if all the prescribed shock pulses have been applied. If shocks still remain, the system returns to step 200. Otherwise, it resets itself.

If no synchronization is achieved in step 210, then in step 214, a check is performed to determine if the pushbuttons 30, 31 are still pressed. If they are not pressed, the system resets in step 218. If the pushbuttons 30, 31 are pressed, then in step 220, a check is performed to determine if a 2.5 second timer has timed out. If it has not timed out then the system returns to step 208 and tries to achieve synchronization again. If the timer has timed out, as indicated in step 220, then in step 222, a shock is applied and the system continues with step 224.

The defibrillator 10 can also be used as a standard manual defibrillator by setting the knob 28 to the manual position. In this position, the knob 28 can be used to select the level of energy for the defibrillation shock. In the manual mode, when the pushbutton 92 is activated, the pulse generator 84 charges its capacitor 84A to the level designated by the knob 28. When the desired level is reached, the lights 30A, 31A are activated and the shock can be applied by depressing the pushbuttons 30, 31.

An important part of the subject invention is the detection of a shockable rhythm (step 152 in FIG. 9). This function is performed by the MDF circuit 80 by analyzing the ECG signal. Primarily, this determination is made from the patient's cardiac rate. However, simply setting a rate threshold to detect tachyarrhythmias is insufficient in some cases because an abnormally high rate (above the threshold) may not be ventricular origin but from other causes such as sinus tachycardia, SVT (supra-ventricular tachycardia), or atrial fibrillation. Shock therapy is not necessarily indicated for these latter arrhythmias and may even be harmful to the patient. In the present invention, the ECG is analyzed and both its magnitude and frequency characteristics are taken into account to distinguish, if possible, VT from other SVT arrhythmias including atrial fibrillation/flutter as well as sinus tachycardia.

More specifically, the present inventors have analyzed and compared the morphologies of VT and SVT rhythms in order to discriminate them. It should be noted that ventricular tachyarrhythmias are characterized by relatively low frequency components, as compared to SVT arrhythmias. Frequency alone may not be adequate for the purposes of this invention. Amplitude must also be taken into account because it fluctuates widely during an arrhythmia episode. However, an amplitude consideration alone (for example, measuring the duration during which the subject wave-shape is above a baseline) has been found to be unsatisfactory because of the inability to detect VT accurately.

Therefore, in the present invention, a procedure has been found which takes both frequency and amplitude into consideration and hence it is referred to as MDF or modulation domain function. The method and apparatus for detecting a shockable event herein has been designed to reduce the probability of delivering therapy for an SVT condition even if its characterized by a rate which is higher than the threshold value Rmin.

Figure 12:
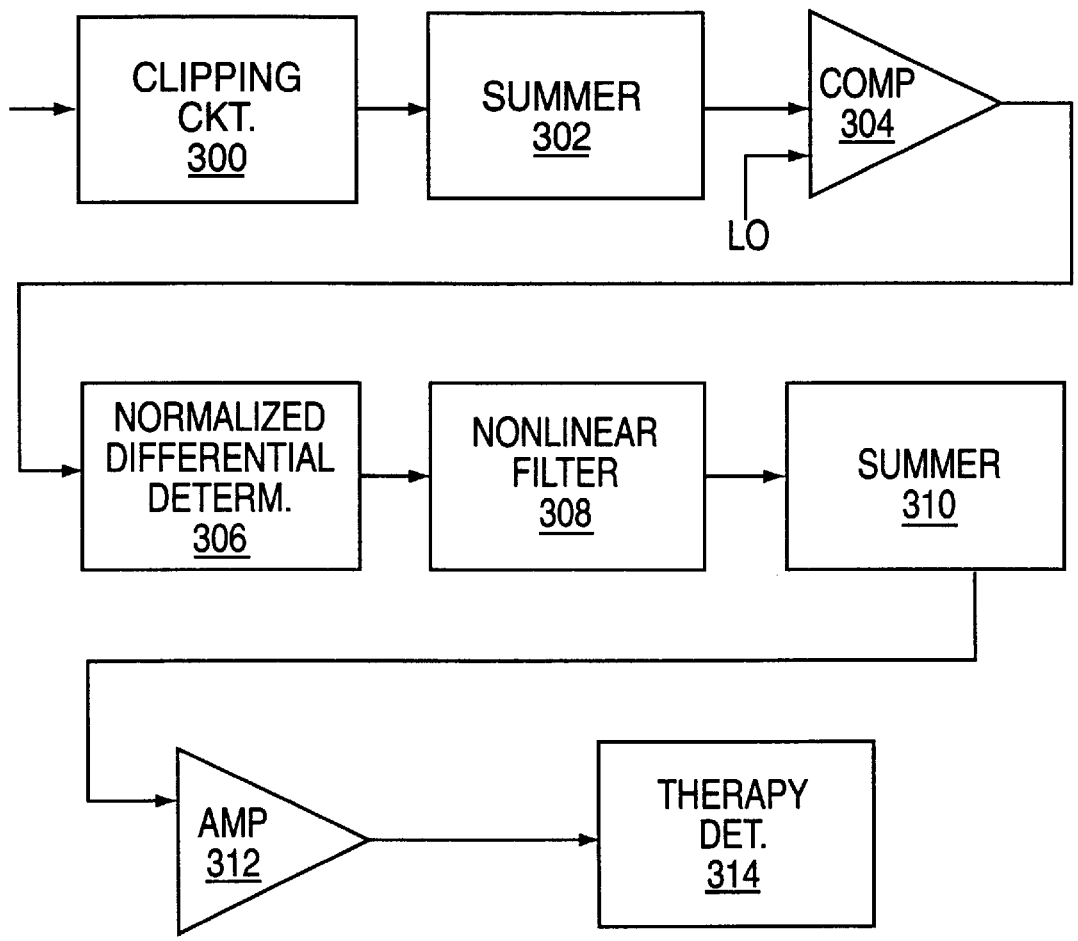
FIG. 12 shows a block diagram for the tachycardia detector circuit of FIG. 5.

Referring now to FIG. 12, the MDF circuit 80 includes a clipping circuit 300, a first summing circuit 302, a comparator 304, a differential normalizing element 306, a non-linear filter 308, a second summer 312, and a second comparator 310.

Figure 13:
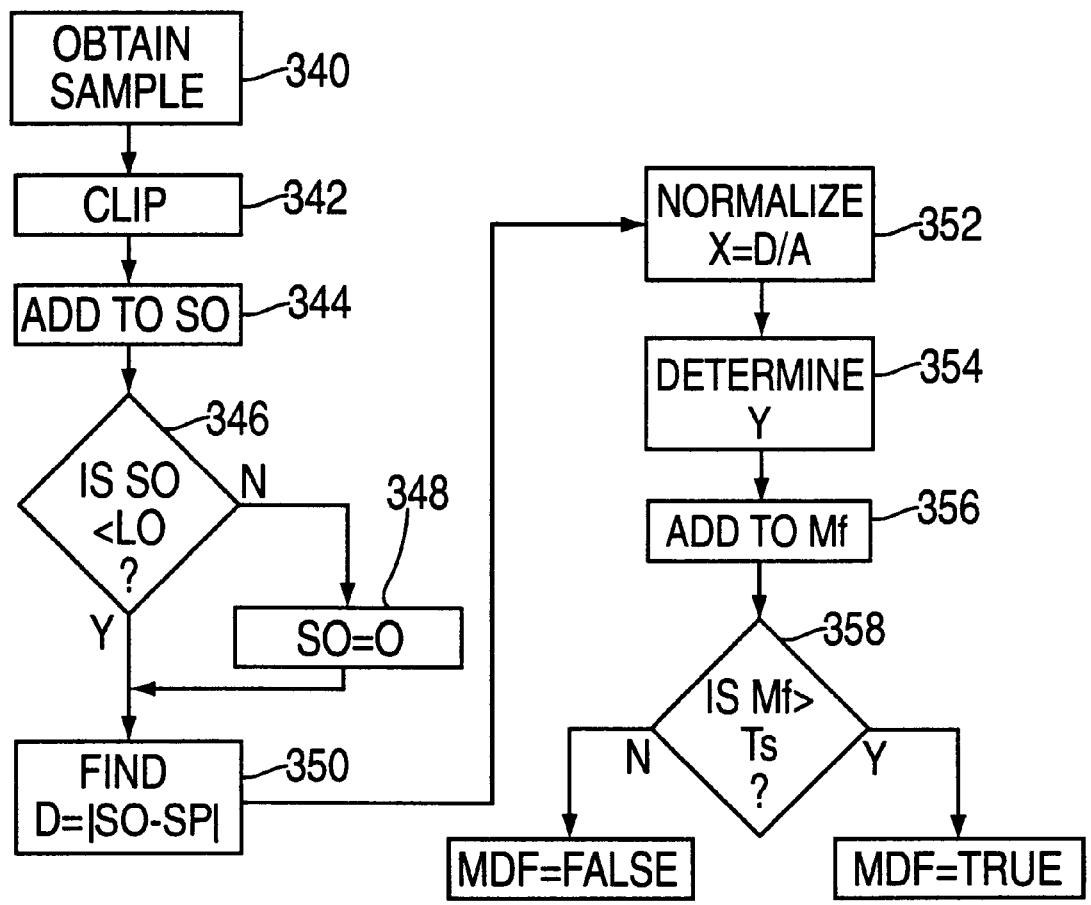
FIG. 13 shows a flow chart illustrating the operation of the circuit of FIG. 12.

The operation of the circuit shown in FIG. 12 will now be described in conjunction with the flow chart of FIG. 13. The circuit 78 receives from circuit 76 (both shown in FIG. 5) a stream of digital signals Ai representative of the current ECG. As each digital signal is received (step 340), it is first clipped by clipping circuit 300 so that it does not exceed a predetermined maximum value (step 342). This step insures that abnormally large values do not unbalance the evaluation performed by the circuit 80. After clipping, the signals Ai are fed to the summer 302. The summer 302 generates a running sum S0 (step 344) of all the digital signals received over the period T. Typically, T may be about 64 milliseconds.

Next, in step 346 the running sum S0 is compared to a threshold value L0 by comparator 304. If S0 is below threshold value L0 then S0 is set to zero (step 348) to insure that any baseline noise existing in the ECG signal does not contribute to the summation.

Next, a normalized differential parameter X is determined by element 306 as follows. First a differential parameter D is determined using the relation:

$$D=|S0-SP|$$

where S0 is the current sum from summer 302 and SP is the immediate previous sum, i.e., before the current digital signal Ai has been processed by the summer 302. The parameter D is then is normalized in step 352 by dividing it by the digital signal Ai to obtain the parameter X (ie., X=D/Ai). The purpose of this step is to reduce the effect of any sudden amplitude changes in the signals Ai.

The parameter X is then fed to filter 308 which is a non-linear filter that uses four preselected parameters to perform a specific filtering function (step 354) to generate a filtered parameter Y. This parameter Y is related to X as follows:

| X | Y |
| --- | --- |
| $X \leq B0$ | 0 |
| $B0 < X \leq B1$ | X |
| $B1 < X \leq B2$ | B1 |
| $B2 < X \leq B3$ | B1*(B3-X)/(B3–B2) |
| $B3 < X$ | 0 | where B0<B1<B2<B3. Typical values for these constants may be 10, 50, 160, and 220 respectively.

The parameter Y is fed to the summer 310. The summer 310 in step 356 generates a running sum of all the values of Y received for the last N seconds. For instance, N may be 4 seconds. The resulting parameter Mf is fed to comparator 312. This comparator 312 generates a parameter MDFi as follows. In step 358 the parameter Mf is compared to a threshold Ts. If Mf is greater than Ts then the comparator 312 generates an MDFi which is true. Otherwise MDFi is false.

One of the programmable options of the defibrillator 10 is the selective enablement of the MDF circuit 80. That is, during the initialization of the defibrillator 10, the attendant has the choice of activating the circuit 80, in which care the parameter MDFi is determined as described above, or the function can be disabled, in which care the MDFi is ignored.

Referring back to FIG. 5, the parameter MDFi is fed to the therapy selector 82. This elector 82 monitors the current cardiac rate Rcur and parameter MDFi (if applicable) and determines whether therapy is required, and if so, then what kind of therapy should be applied.

Figure 14:
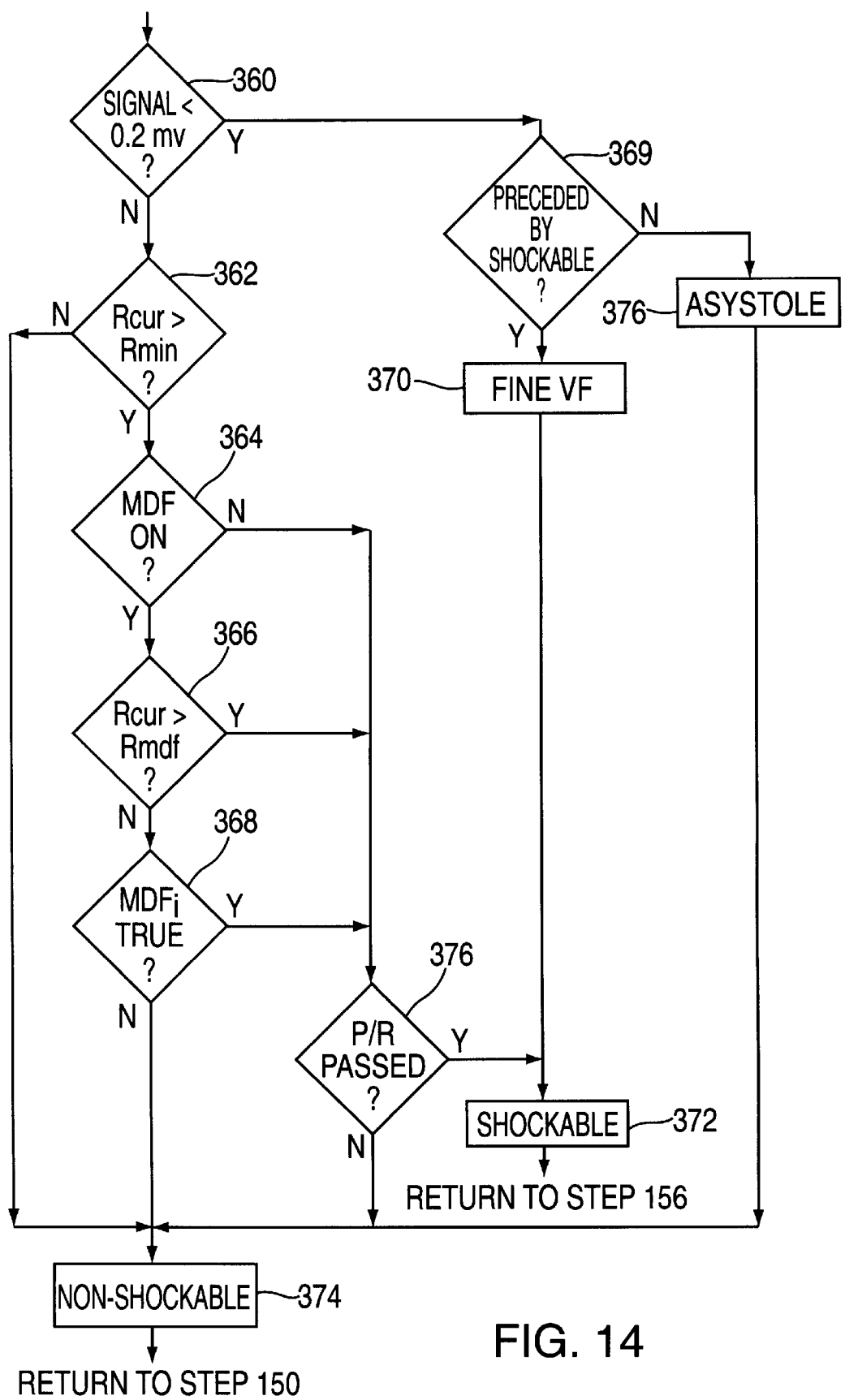
FIG. 14 shows a flowchart illustrating the operation of the therapy selector of FIG. 5.

Referring to FIG. 14, in step 360, a check is performed to determine if the peak to peak amplitude of the signal obtained in step 150 (FIG. 9) is less than 0.2 milli-volts for the last 8 seconds. If it does, the algorithm checks to see if a shockable rhythm has been detected prior to this latter period (Step 369). if a shockable rhythm has been detected, the algorithm classifies the rhythm as Fine VF (Step 370) which is shockable (Step 372). If a shockable rhythm has not been detected, the algorithm classifies the rhythm as asystole (Step 376) which is not considered a schockable rhythm (Step 374).

In step 362, the current rate Rcur from step 150 is first checked to see if it exceeds the minimum rate Rmin. If it does not, then the rhythm is classified as non-shockable (Step 374) and monitoring of the heart continues in step 150 without any therapy. In step 364, a check is performed to determine if the MDF mode has been activated. If it is not, it continues to step 366. If this mode has been activated, a check is performed in step 366 to determine if Rcur is greater than Rmdf. If it is, the algorithm continues to step 368. In step 368, a check is performed to determine if the parameter MDFi is true. If it is true, the algorithm continues to step 376. If MDFi is not true, the rhythm is classified as non-shockable (Step 374) and no therapy is performed at this time. In step 376, a P of R test is performed during which P of the last R intervals must correspond to a rate higher than Rmin. For example, P could be 4 and R could be 6. If the test failed, the rhythm is classified as non-shockable (Step 374), and the algorithm returns to step 150.

If the P of R test is passed, then the current rate Rcur is designated as a shockable rhythm corresponding to ventricular tachyarrhythmias and the process continues to step 156 in FIG. 9.

In summary, the microprocessor 70, rate detector 78, MDF circuit 80 and the therapy selector 82 cooperate to determine if the current cardiac condition of the patient should be classified as a shockable rhythm or not based on the current rate Rcur as well as the amplitude and frequency of the ECG signals. If the rate Rcur is below the threshold Rmin, no therapy is applied. If the rate is above Rmin, a determination is made as to whether the rhythm is shockable or not, based the parameters and modes described. Since VT and ventricular fibrillation could be life-threatening, it is preferably that a conservative approach be taken when selecting these parameters.

The process and apparatus described above and in FIGS. 12 and 13 is primarily designed for use in the automatic external cardioverter defibrillator, however it may also be used in internal cardioverter/defibrillator devices and other cardiac devices as well.

Obviously, numerous modifications may be made to this invention without departing from its scope as defined in the appended claims.

We claim:

1. An external defibrillator that can be used to apply therapy to a patient, comprising:

an electrode adapted to couple externally to the body of a patient;

a sense circuit coupled to said electrode to sense a physiological signal of the patient indicative of intrinsic cardiac activity;

a cardiac arrhythmia detector coupled to said sense circuit to detect a life threatening cardiac arrhythmia based on said physiological signal;

a modulation domain function detector that analyzes said physiological signal to detect its frequency and amplitude and generates a parameter indicative of a cardiac condition of the patient dependent on said frequency and amplitude;

wherein said cardiac arrhythmia detector is arranged and constructed to generates serially samples of said physiological signal and said modulation domain function detector includes a summer which adds a predetermined number of said samples to generate a sum and a comparator adapted to compare said sum to a predetermined threshold, wherein said summer is arranged and constructed to generate a parameter indicative of a duration of said physiological signal;

a microprocessor-based controller adapted to generate automatically a command in the presence of said cardiac arrhythmia and in accordance with said parameter; and a therapy delivery circuit adapted to deliver electrical therapy pulses to said patient to correct said cardiac arrhythmia in response to said command.

2. The defibrillator of claim 1 wherein said detector circuit is adapted to generate a sense signal indicative of an ECG complex, and said summer is adapted to generate said parameter with said parameter being related to a duration of said ECG complex.

3. The defibrillator of claim 1 further comprising a mode selector which can be activated by an attendant for selectively disabling said modulation domain function detector.

4. An external defibrillator for automatically generating a cardiac therapy for a person suffering from a life threatening cardiac condition, said external defibrillator comprising:

a first electrode adapted to be attached to said patient to sense intrinsic cardiac signals from the patient;

a modulation domain function detector coupled to said electrode to receive said cardiac signals and to generate a corresponding control parameter, said control parameter being generated to differentiate between ventricular arrhythmia and fibrillation, wherein said modulation domain function detector includes a first summer that sums samples from the intrinsic signals taken over a time period, a normalizer for normalizing said sum to compensate for amplitude variations of said intrinsic signals, said normalizer generating a normalized signal related to said parameter;

a detector circuit coupled to said first electrode and adapted to detect a life threatening cardiac condition based on a physiological signal sensed through said electrode and said control parameter;

a microprocessor-based controller coupled to said detector circuit and adapted to generate a command in the presence of said life threatening condition; and a pulse generator adapted to generate therapeutic pulses selected to terminate said life threatening cardiac condition in response to said command.

5. The external defibrillator of claim 4 further comprising a second electrode attached to said patient and being coupled to said pulse generator to deliver said therapeutic pulses to the patient's heart.

6. The external defibrillator of claim 4 further comprising a sensor circuit coupled to said first electrode to sense intrinsic cardiac signals, said sensor circuit being adapted to transmit said intrinsic cardiac signals to said detector circuit.

7. The external defibrillator of claim 4 wherein said modulation domain detector includes a duration detector that determines the duration of a particular cardiac complex, said parameter being related to said duration.

8. The external defibrillator of claim 4 wherein said detector circuit is adapted to detect intrinsic cardiac signals and said controller is adapted to generate said command in synchronism with said intrinsic cardiac signals.

9. The external defibrillator of claim 8 wherein said detector circuit is adapted to detect R-waves and said controller is adapted to generate said command at a predetermined interval after said R-waves.

10. The external defibrillator of claim 9 wherein said controller is adapted to delay said command after said R-wave, said delay being selected to insure that said therapeutic pulses do not coincide with a T-wave.

11. The external defibrillator of claim 4 wherein said modulation domain function detector further includes a non-linear filter that filters said normalized signal to generate a filtered signal.

12. The external defibrillator of claim 11 wherein said modulation domain function detector further includes a second summer that sums said filtered signal.

13. The external defibrillator of claim 12 further comprising a comparator that compares said filtered signal to a threshold value, said parameter being dependent on the output of said comparator.

14. The external defibrillator of claim 4 further comprising an inhibit switch which may be used to inhibit the operation of said modulation domain function detector.

15. An external defibrillator that can be used to apply therapy to a patient, comprising:
   an electrode adapted to couple externally to the body of a patient;
   a sense circuit coupled to said electrode to sense a physiological signal indicative of an ECG complex of the patient;
   a cardiac arrhythmia detector coupled to said sense circuit to detect a life threatening cardiac arrhythmia based on said physiological signal;
   a modulation domain function detector that analyzes said physiological signal to detect its frequency and amplitude and generates a parameter indicative of a cardiac condition of the patient dependent on said frequency and amplitude;
   wherein said cardiac arrhythmia detector is arranged and constructed to generates serially samples of said physiological signal and said modulation domain function detector includes a summer which adds a predetermined number of said samples to generate a sum and a comparator adapted to compare said sum to a predetermined threshold, wherein said summer is arranged and constructed to generate a parameter related to a duration of said ECG complex;
   a microprocessor-based controller adapted to generate automatically a command in the presence of said cardiac arrhythmia and in accordance with said parameter; and
   a therapy delivery circuit adapted to deliver electrical therapy pulses to said patient to correct said cardiac arrhythmia in response to said command.

16. An external defibrillator that can be used to apply therapy to a patient, comprising:
   an electrode adapted to couple externally to the body of a patient;
   a sense circuit coupled to said electrode to sense a physiological signal indicative of an ECG complex of the patient;
   a cardiac arrhythmia detector coupled to said sense circuit to detect a life threatening cardiac arrhythmia based on said physiological signal;
   a modulation domain function detector that analyzes said physiological signal to detect its frequency and amplitude and generates a parameter indicative of a cardiac condition of the patient dependent on said frequency and amplitude;
   a microprocessor-based controller adapted to generate automatically a command in the presence of said cardiac arrhythmia and in accordance with said parameter;
   a therapy delivery circuit adapted to deliver electrical therapy pulses to said patient to correct said cardiac arrhythmia in response to said command; and
   a mode selector which can be activated by an attendant for selectively disabling said modulation domain function detector.

17. An external defibillator for automatically generating a cardiac therapy for a person suffering from a life threatening cardiac condition, said external defibrillator comprising:
   an electrode adapted to be attached to said patient to sense intrinsic cardiac signals from the patient;
   a modulation domain function detector coupled to said electrode to receive said cardiac signals and to generate a corresponding control parameter, said control parameter being generated to differentiate between ventricular arrhythmia and fibrillation, wherein said modulation domain function detector includes a modulation detector that determines the duration of a particular cardiac complex, said control parameter being a function of said duration;
   a detector circuit coupled to said first electrode and adapted to detect a life threatening cardiac condition based on a physiological signal sensed through said electrode and said control parameter;
   a microprocessor-based controller coupled to said detector circuit and adapted to generate a command in the presence of said life threatening condition; and
   a pulse generator adapted to generate therapeutic pulses selected to terminate said life threatening cardiac condition in response to said command.

18. An external defibrillator for automatically generating a cardiac therapy for a person suffering from a life threatening cardiac condition, said external defibrillator comprising:
   a first electrode adapted to be attached to said patient to sense intrinsic cardiac signals from the patient;
   a modulation domain function detector coupled to said electrode to receive said cardiac signals and to generate a corresponding control parameter, said control parameter being generated to differentiate between ventricular arrhythmia and fibrillation based on the amplitude and frequency of said intrinsic signals;
   a detector circuit coupled to said first electrode and adapted to detect a life threatening cardiac condition based on a physiological signal sensed through said electrode and said control parameter;
   a microprocessor-based controller coupled to said detector circuit and adapted to generate a command in the presence of said life threatening condition;
   a pulse generator adapted to generate therapeutic pulses selected to terminate said life threatening cardiac condition in response to said command; and
   an inhibit switch that may be used to inhibit the operation of said modulation domain function detector.

* * * * *